United States Patent

Carsten et al.

[11] Patent Number: 5,614,050
[45] Date of Patent: Mar. 25, 1997

[54] METHOD AND ARTICLE FOR PRODUCING FLEXIBLE, FLAT SUBSTRATES WITH POROUS ADHESIVE COATINGS

[75] Inventors: Rolf Carsten, Hamburg; Rolf Schulze, Kasseedorf; Axel von Wolff, Hamburg, all of Germany

[73] Assignee: Beiersdorf Aktiengesellschaft, Hamburg, Germany

[21] Appl. No.: 256,699

[22] PCT Filed: Feb. 3, 1992

[86] PCT No.: PCT/DE92/00065

§ 371 Date: Oct. 4, 1992

§ 102(e) Date: Oct. 4, 1992

[87] PCT Pub. No.: WO93/14725

PCT Pub. Date: Aug. 5, 1993

[51] Int. Cl.$^6$ ................................................ B29B 13/00
[52] U.S. Cl. .................. 156/231; 156/238; 156/209; 264/284; 264/309; 427/208.6; 604/307
[58] Field of Search ................................. 156/231, 230, 156/235, 238, 209; 604/304, 307, 387; 427/207.1, 208.4, 208.6; 264/284, 309, 214

[56] References Cited

U.S. PATENT DOCUMENTS

| 3,471,354 | 10/1969 | Scofield | 264/284 |
|---|---|---|---|
| 3,523,846 | 8/1970 | Muller | 156/231 X |
| 3,650,882 | 3/1972 | Thomas. | |
| 3,908,650 | 9/1975 | Dunshee et al. | 604/387 X |
| 3,991,754 | 11/1976 | Gertzman | 604/387 |
| 4,163,822 | 8/1979 | Walter | 156/230 X |
| 4,302,500 | 11/1981 | Flora | 156/235 X |
| 4,789,413 | 12/1988 | Tani et al. | 156/231 X |
| 4,844,766 | 7/1989 | Held | 264/284 X |

FOREIGN PATENT DOCUMENTS

| 952945 | 10/1956 | Germany | 264/309 |
|---|---|---|---|
| 546485 | 7/1956 | Italy | 264/284 |
| 38-4491 | 4/1963 | Japan | 156/209 |
| 45-4439 | 2/1970 | Japan | 427/208.4 |
| 1-258934 | 10/1989 | Japan | 264/284 |
| 4-175390 | 6/1992 | Japan | 427/208.6 |
| 479795 | 2/1938 | United Kingdom | 427/208.6 |

*Primary Examiner*—David A. Simmons
*Assistant Examiner*—Paul M. Rivard
*Attorney, Agent, or Firm*—Sprung Horn Kramer & Woods

[57] ABSTRACT

Process for producing a flexible, planar carrier coated with a porous adhesive layer, characterized in that a) a flowable adhesive composition is applied to an intermediate carrier having the following properties:
  it has a microscopically undulating, pleated, fissured or furrowed surface
  the adhesive composition can be easily detached from the surface thereof
  it is essentially air-impermeable, b) the microscopic air or solvent inclusions resulting, after coating the intermediate carrier, between the adhesive composition and the intermediate carrier are expanded by increasing the temperature until the surface of the adhesive composition bursts, and c) the adhesive composition is subsequently transferred from the intermediate carrier onto the final carrier.

6 Claims, No Drawings

METHOD AND ARTICLE FOR PRODUCING FLEXIBLE, FLAT SUBSTRATES WITH POROUS ADHESIVE COATINGS

BACKGROUND OF THE INVENTION

The invention relates to processes for coating carrier materials with adhesives and to products obtainable by means of such processes. In particular it relates to processes for coating planar carriers such as, for example, fabric tapes, non-woven fabrics, paper tapes or plastic tapes.

Adhesive-coated carriers, at least planar carriers, are known per se and are widespread. Thus, adhesive-coated plastic tapes and paper tapes have for a long time been a routine aid in offices and homes. The consumer has also become aware of self-adhesive plasters, as quick wound dressings, for many decades in a variety of forms.

In many cases the carriers consist of non-occlusive material, that is to say they are highly permeable for water vapour and/or air. In many cases this is desirable, since in by far the majority of cases the more permeable a quick wound dressing is to air and moisture, the better is its skin compatibility.

However, in order to make the adhesive coating non-occlusive, inconvenient, impractical and usually highly uneconomic processes had to be used in the past.

It is known to provide the carrier with an adhesive application which is limited in surface area or interrupted by adhesive-free places. It is also known subsequently to perforate the material coated with the adhesive composition, for example with the aid of air nozzles.

However, these processes are unsuitable for producing microporous adhesive layers with really satisfactory properties.

Furthermore German Patent 15 69 901 discloses the following process for producing porous, self-adhesive tapes or sheets: a solvent-containing viscoelastic self-adhesive composition is applied onto an intermediate carrier with an adhesive-repellent surface, the temperature is rapidly increased so that the solvent or dispersant evaporates and the viscoelastic self-adhesive composition forms bubbles. After the adhesive layer is dry, the intermediate carrier coated in this manner is pressed against a porous substrate, that is to say a planar carrier. The self-adhesive composition is thus transferred to the substrate. The elevated pressure has the effect that the bubbles burst and fine pores result.

Although the adhesive layers formed in this manner are microporous, by no means all bubbles burst. As regards its theoretically expected results, the process described here thus does not function in an optimum manner.

In addition, the paper carrier used is not indefinitely reusable. The process is thus expensive.

German Offenlegungsschrift 36 06 199 describes an adhesive label having an adhesive layer whose surface has, within a region provided with the adhesive layer over an essentially continuous area, elevations and depressions. It is not porous or even microporous adhesive layers which are described, but continuous-area coatings.

The surface structuring which is described in this publication is macroscopic in nature.

Neither air nor solvent vapours from the intermediate carrier and adhesive layer are enclosed by this surface structure. Rather, it is only achieved that the adhesive layer is thicker in one place and thinner at another place, assuming an undulating surface.

It is also apparent that the self-adhesive objects conceived here are remote from any medical use, since not only do they lift easily off the substrate, but also, because they are not porous, they occlude the substrate.

German Offenlegungsschrift 27 19 779 relates to a self-adhesive, porous, air-permeable strip for use as dressing material. The pores are produced in that a blowing agent which is dissolved in the adhesive composition is heated and thereby expands. The blowing agent bubbles thus produced are intended to tear open the adhesive layer. Blowing agents are described in this publication which can be entirely dispensed with according to the present invention. In the only example, $NH_4O_3$, which is also a component of baking powder, is specified as blowing agent. The risk of the ammonia resulting from the thermal decomposition of $NH_4CO_3$ under-going undesirable secondary reactions, for example with the adhesive composition itself or else with the carrier is too high. In addition, the $NH_4CO_3$ which is present as solid must be elaborately ground and uniformly distributed in the adhesive composition.

In addition, it is to be expected that the $NH_4CO_3$ sediments in the adhesive composition, that is to say uniform blowing agent distribution is not achieved. Sedimentation is a well known unwelcome side effect of the dispersion of pulverulent solids in adhesive compositions. Zones with high solid agglomeration and zones with low solid content occur.

Although pressure treatment analogous to German Auslegeschrift 15 69 901 is neither described nor claimed, the person skilled in the art knows that the blowing agent more or less uniformly distributed in the adhesive composition—in addition to occasionally occurring pores—mainly forms closed bubbles. The latter must be opened by mechanical action.

SUMMARY OF THE INVENTION

It was thus the object of the present invention to develop a process with the aid of which microporous adhesive layers can be obtained in an economical manner without the process or the products having the deficiencies of the prior art.

According to the invention the object is achieved by a process for producing a flexible, planar carrier coated with a porous adhesive layer, characterized in that a) a flowable adhesive composition is applied onto an intermediate carrier having the following properties:
   it has a microscopically undulating, pleated, fissured or furrowed surface
   the adhesive composition can be easily detached from the surface thereof,
   it is substantially air-impermeable, b) the microscopic air or solvent inclusions resulting, after coating the intermediate carrier, between the adhesive composition and the intermediate carrier are expanded by increasing the temperature until the surface of the adhesive composition bursts, and c) the adhesive composition is subsequently transferred from the intermediate carrier onto the final carrier.

By the term "microscopically undulating, pleated, fissured or furrowed surface", within the scope of this application, it is meant that the surface of the intermediate carrier is not intended to be smooth, but rather has irregular or regular elevations and/or depressions. This structure should be detectable under optical or electron microscopic enlargement. It is especially advantageous if the surface of the intermediate carrier, seen microscopically, resembles orange peel or a hilly landscape.

According to the present invention, the porosity is obtained in that air between the adhesive layer and the intermediate carrier breaks through the adhesive layer by expanding.

Due to the advantageous properties of the present invention, a post-treatment, namely the exertion of an additional mechanical pressure on the carrier, so that the pores form at all is entirely unnecessary.

It should be observed according to the invention that, on application, the adhesive composition should not completely fill the depressions of the intermediate carrier but that between the adhesive composition and the intermediate carrier hollow spaces form which are filled with air and/or solvent vapour.

The person skilled in the art knows how the viscosity of adhesive compositions can be influenced and is quite capable of adapting the viscosity of the microscopically undulating, pleated, fissured or furrowed surface by simple trial.

It is especially advantageous to choose the adhesive composition from the group of conventional self-adhesive compositions, in particular pressure-sensitive self-adhesive compositions. The carriers can advantageously be selected from the group comprising non-woven fabric, fabric sheets, paper sheets or plastic films or the like.

The porous adhesive layers which can be obtained by this process and also planar carriers coated with such adhesive layers are also advantageous embodiments of the present invention. This applies in particular to those adhesive layers which are characterized by:

an average hole distribution of 10–30 holes/mm$^2$ an average hole size of 15–75 µm.

The intermediate carriers with microscopically undulating, pleated, fissured or furrowed surface are advantageously obtained by coating a flexible basic body of durable material with a polymeric plastic. It is favourable first to apply the plastic and to provide the plastic, before curing, with a surface structure according to the invention by means of a surface-structured object, for example a circulating foam belt or a foam roll. If the plastic is first applied and then structured, all coating processes can in principle be used, for example also a spraying process.

However, it is also possible and advantageous to carry out the coating itself using a surface-structured device, in particular an absorbent, particularly preferably a porous, device such as a foam roll for example. With this type of coating, the surface of the plastic takes on the structure according to the invention without further treatment.

DETAILED DESCRIPTION OF THE PREFERRED EMBODIMENT

Accordingly, the following are regarded as according to the invention: a process for producing an intermediate carrier, which intermediate carrier can be obtained in that a plastic present in liquid form is applied by means of a surface-structured device, in particular an absorbent, particularly preferably a porous, device, for example a foam roll, onto a flexible basic body, and a process for producing an intermediate carrier, which can be obtained in that a plastic present in liquid form is applied onto a flexible basic body and the plastic, before curing, is provided with a surface structure by means of a surface-structured device, in particular an absorbent, particularly preferably a porous, device, for example a foam roll or a circulating foam belt.

It is favourable to allow the coated and surface-structured intermediate carrier to dry out in a drying system.

Intermediate carriers obtainable by such processes, and also an intermediate carrier with the features that it has a microscopically undulating, pleated, fissured or furrowed surface the adhesive composition can be easily detached from the surface thereof it is essentially air-impermeable are equally regarded as embodiments of the present invention.

The basic body for the intermediate carriers can be chosen from all materials customary for such purposes. Woven belts made of glass fibres are especially advantageous. However, rubber blankets, plastic webs and the like have also proved favourable. If glass fibre belts are chosen, it is favourable to use those which are already provided with an essentially unstructured surface coating of plastic. The latter coating promotes the adhesion of the plastic coating according to the invention with a surface structure on the basic body.

The plastics with which the intermediate carriers are coated can advantageously be chosen from the group comprising silicone rubbers, even though other durable plastics come into consideration as well. These plastics can be applied onto the intermediate carrier using the conventional coating processes, for example by means of knife coating. It is advantageous to use the plastics in dissolved form. Nevertheless, it may be advantageous to use the plastics in an undissolved form if they are themselves flowable.

The following examples are intended to explain the invention in greater detail without, however, the intention of restricting the invention to these examples. Rather, the person skilled in the art is capable by means of his specialist knowledge of carrying out modifications which do not depart from the scope of the present invention.

EXAMPLE 1

Production of a surface-structured intermediate carrier:

A woven glass fibre belt with transparent silicone coating (coating thickness approximately 0.5 mm, total thickness approximately 2 mm) is coated with silicone rubber, by means of a knife-coating process:

An acetate-curing permanently flexible silicone rubber with Shore hardness>25, density of 1.0–1.15 kg/m$^3$ is used. It is diluted to a suitable viscosity using naphtha 60/95.

This solution is applied to the glass fibre belt using a coating knife. Closely behind the coating knife, the surface of the silicone rubber is post-treated by means of a foam roll.

The glass fibre belt coated in this manner is passed through a 9 m long nozzle dryer at a web speed of 1.5 m/min at 100° C. After final drying (24 hours at room temperature) the intermediate carrier is ready for use.

EXAMPLE 2

Coating of a flexible carrier with a self-adhesive composition

An intermediate carrier according to Example 1 is coated by the so-called blanket coating process using a doctor knife system with a viscoelastic self-adhesive composition which was obtained by copolymerizing 490 parts by weight of 2-ethylhexyl acrylate, 490 parts by weight of n-butyl acrylate and 20 parts by weight of glycidyl methacrylate from solution in an acetone-naphtha mixture in an amount corresponding to a layer thickness of approximately 45 g/m$^2$ after drying. The intermediate carrier now covered with the self-adhesive composition is guided at a speed of approximately 15 m/min. through a drying tunnel which can be heated by stages and is subdivided into six heating zones having the following temperatures: 100°/100°/100°/100°/90°/80° C.

During drying the air (or the solvent vapour/air mixture) between the surface of the intermediate carrier and the self-adhesive composition expands and causes the adhesive layer to burst at the affected points.

The now finely perforated adhesive layer is laminated by means of pressure rolls onto a random laid non-woven fabric (viscose, approximately 30 g/m$^2$).

The finished random laid non-woven fabric coated in a microporous manner can be cut into strips of the desired width and wound on rolls. In order to facilitate unwinding, it may be advantageous to cover the reverse side of the carrier used (in this case the random laid non-woven fabric), which is not coated with the self-adhesive composition, with a layer of adhesive-repellent material.

EXAMPLE 3

Coating of a perforated film with self-adhesive composition

An intermediate carrier according to Example 1 is coated by the so-called blanket coating process using a doctor knife system with a viscoelastic self-adhesive composition which was obtained by copolymerizing 490 parts by weight of 2-ethylhexyl acrylate, 490 parts by weight of n-butyl acrylate and 20 parts by weight of glycidyl methacrylate from solution in an acetone-naphtha mixture in an amount corresponding to a layer thickness of approximately 45 g/m$^2$ after drying. The intermediate carrier now covered with the self-adhesive composition is guided at a speed of approximately 15 m/min. through a drying tunnel which can be heated by stages and is subdivided into six heating zones having the following temperatures: 100°/100°/100°/100°/90°/80° C.

During drying, the air between the surface of the intermediate carrier and the self-adhesive composition expands and causes the adhesive layer to burst at the affected places.

The adhesive layer which is now finely perforated is laminated by means of pressure rolls onto a perforated film. The finished film coated in a microporous manner can be cut into strips of the desired width and wound on rolls.

EXAMPLE 4

Coating a fabric web with self-adhesive composition

An intermediate carrier according to Example 1 is coated by the so-called blanket coating process using a doctor knife system with a viscoelastic self-adhesive composition which was obtained by copolymerizing 490 parts by weight of 2-ethylhexyl acrylate, 490 parts by weight of n-butyl acrylate and 20 parts by weight of glycidyl methacrylate from solution in an acetone-naphtha mixture in an amount corresponding to a layer thickness of approximately 45 g/m$^2$ after drying. The intermediate carrier now covered with the self-adhesive composition is guided at a speed of approximately 10 m/min. through a drying tunnel which can be heated by stages and is subdivided into six heating zones having the following temperatures: 100°/100°/100°/100°/90°/80° C.

During drying, the air between the surface of the intermediate carrier and the self-adhesive composition expands and causes the adhesive layer to burst at the affected places.

The now finely perforated adhesive layer is laminated by means of pressure rolls onto an elastic woven fabric (approximately 300 g/m$^2$). The final fabric coated in a microporous manner can be cut into strips of the desired width and wound on rolls.

We claim:
1. Process for producing a flexible, planar carrier coated with a porous adhesive layer, characterized in that
    a) a flowable adhesive composition is applied onto an intermediate carrier having the following properties:
        it has a microscopically undulating, pleated, fissured or furrowed surface
        the adhesive composition can be easily detached from the surface thereof
        it is essentially air-impermeable, the intermediate carrier comprising a flexible basic body onto which plastic in liquid form was applied by means of a suitably surface-structured foam roll or foam web, thereby imparting the microscopically undulating, pleated, fissured or furrowed surface,
    b) microscopic air or solvent inclusions resulting, after coating the intermediate carrier, between the adhesive composition and the intermediate carrier, which inclusions are expanded by increasing the temperature until the surface of the adhesive composition bursts, and
    c) the adhesive composition is subsequently transferred from the intermediate carrier onto the final carrier.
2. Process for producing a flexible, planar carrier coated with a porous adhesive layer, characterized in that
    a) a flowable adhesive composition is applied onto an intermediate carrier having the following properties:
        it has a microscopically undulating, pleated, fissured or furrowed surface
        the adhesive composition can be easily detached from the surface thereof
        it is essentially air-impermeable, the intermediate carrier comprising a flexible basic body onto which plastic was sprayed, a foam roll or foam web contacting the spray-coating, thereby imparting the microscopically undulating, pleated, fissured or furrowed surface,
    b) microscopic air or solvent inclusions resulting, after spraying the intermediate carrier, between the adhesive composition and the intermediate carrier, which inclusions are expanded by increasing the temperature until the surface of the adhesive composition bursts, and
    c) the adhesive composition is subsequently transferred from the intermediate carrier onto the final carrier.
3. Process for producing a flexible, planar carrier coated with a porous adhesive layer, characterized in that
    a) a flowable adhesive composition is applied onto an intermediate carrier having the following properties:
        it has a microscopically undulating, pleated, fissured or furrowed surface
        the adhesive composition can be easily detached from the surface thereof
        it is essentially air-impermeable,
    b) microscopic air or solvent inclusions resulting, after coating the intermediate carrier, between the adhesive composition and the intermediate carrier, which inclusions are expanded by increasing the temperature until the surface of the adhesive composition bursts, and
    c) the adhesive composition is subsequently transferred from the intermediate carrier onto the final carrier, the intermediate carrier's surface in combination with the flowable adhesive composition having trapped bubbles of air or solvent between said surface and composition which bubbles upon drying of the coated intermediate carrier burst and form holes in the dried adhesive of an average size of 50–75 μm and an average distribution of 10–30 holes/mm².

4. The product produced by the process of claim 3.

5. An intermediate carrier having the following properties:

it has a microscopically undulating, pleated, fissured or furrowed surface the adhesive composition can be easily detached from the surface thereof it is essentially air-impermeable, the intermediate carrier comprising a flexible basic body onto which plastic in liquid form was applied by means of a suitably surface-structured foam roll or foam web, thereby imparting the microscopically undulating, pleated, fissured or furrowed surface, whereby in using such intermediate carrier by coating it with a flowable adhesive composition air or solvent inclusions result between the adhesive composition and the intermediate carrier surface.

6. Process for producing a flexible, planar carrier coated with a porous adhesive layer, characterized in that a) a flowable adhesive composition is applied onto an intermediate carrier having the following properties:

it has a microscopically undulating, pleated, fissured or furrowed surface the adhesive composition can be easily detached from the surface thereof it is essentially air-impermeable, the intermediate carrier comprising a flexible basic body onto which plastic was sprayed, a foam roll or foam web contacting the spray-coating, thereby imparting the microscopically undulating, pleated, fissured or furrowed surface, whereby in using such intermediate carrier by coating it with a flowable adhesive composition air or solvent inclusions result between the adhesive composition and the intermediate carrier surface.

* * * * *

UNITED STATES PATENT AND TRADEMARK OFFICE
CERTIFICATE OF CORRECTION

PATENT NO. : 5,614,050

DATED : March 25, 1997

INVENTOR(S) : Carsten, et al.

It is certified that error appears in the above-identified patent and that said Letters Patent is hereby corrected as shown below:

Title Page    371 Date:   Delete " Oct. 4, 1992 and substitute
                          -- Oct. 4, 1994 --

Title Page    102(c) Date:  Delete " Oct. 4, 1992 " and substitute
                            -- Oct. 4, 1994 --

Signed and Sealed this

Twenty-sixth Day of August, 1997

*Attest:*

BRUCE LEHMAN

*Attesting Officer*    *Commissioner of Patents and Trademarks*